(12) United States Patent
Fukushima

(10) Patent No.: US 8,733,354 B2
(45) Date of Patent: May 27, 2014

(54) OXYGEN SUPPLY DEVICE

(75) Inventor: Nobuyuki Fukushima, Saitama (JP)

(73) Assignee: Fukushima O-Two Co., Ltd., Kumagaya (JP)

( * ) Notice: Subject to any disclaimer, the term of this patent is extended or adjusted under 35 U.S.C. 154(b) by 158 days.

(21) Appl. No.: 13/060,562

(22) PCT Filed: Aug. 26, 2009

(86) PCT No.: PCT/JP2009/065278
§ 371 (c)(1),
(2), (4) Date: Feb. 24, 2011

(87) PCT Pub. No.: WO2010/024450
PCT Pub. Date: Mar. 4, 2010

(65) Prior Publication Data
US 2011/0146687 A1    Jun. 23, 2011

(30) Foreign Application Priority Data
Aug. 29, 2008  (JP) ................ 2008-222387

(51) Int. Cl.
*A61M 16/08*       (2006.01)
(52) U.S. Cl.
USPC ............................................. 128/205.25
(58) Field of Classification Search
USPC ............ 128/205.25, 207.11, 200.24, 202.12, 128/202.13, 202.16, 204.18, 205.26; 482/1–142
See application file for complete search history.

(56) References Cited

U.S. PATENT DOCUMENTS

| | | | | |
|---|---|---|---|---|
| 4,619,255 A | * | 10/1986 | Spinosa et al. | 128/202.27 |
| 5,078,343 A | * | 1/1992 | Howlett | 244/118.5 |
| 6,631,719 B2 | * | 10/2003 | McDonald et al. | 128/207.11 |
| 2008/0223369 A1 | * | 9/2008 | Warren | 128/205.25 |

FOREIGN PATENT DOCUMENTS

| | | |
|---|---|---|
| JP | 07-001947 U | 1/1995 |
| JP | 2001-327602 A | 11/2001 |
| JP | 2003-265645 A | 9/2003 |
| JP | 2004-337497 A | 12/2004 |
| JP | 2006-328931 A | 12/2006 |
| JP | 2007-185457 A | 7/2007 |

OTHER PUBLICATIONS

Derwent Document 2008-F57463.*

* cited by examiner

*Primary Examiner* — Tan-Uyen T. Ho
*Assistant Examiner* — Mark Wardas
(74) *Attorney, Agent, or Firm* — Kubotera & Associates, LLC

(57) ABSTRACT

An oxygen supply device includes: an oxygen tank (10); a pipe (20) which is connected to the oxygen tank; an oxygen mask (30); and a joint (40) which detachably connects the oxygen mask to the pipe, wherein the joint includes a socket (41) provided for the pipe and a plug (42) provided for the oxygen mask, wherein the oxygen mask includes a head attachment portion (31) attached to a head of the user, a pipe body (32) supported by the head attachment portion and having a front end portion extending toward the front side of the head of the user, and a tube (33) connecting a base end portion of the pipe body to the plug (42), and wherein the socket is provided for each component of the pipe, and the plug is connectable to each socket.

5 Claims, 3 Drawing Sheets

OXYGEN SUPPLY DEVICE

TECHNICAL FIELD

The present invention relates to an oxygen supply device to be provided in a facility such as a sports center or a training gym for fitness activities.

BACKGROUND ART

In regard with an exercise for keeping or improving health or physical strength, that is, a fitness activity, a function of a heart or a lung may be improved by the amount of oxygen absorbed into a body. For example, Patent Documents 1 and 2 disclose a training machine having a configuration in which oxygen is supplied to a training person.

Further, as an oxygen supply device provided at a predetermined facility, there is known a configuration in which oxygen is supplied to users through a pipe provided in the facility. According to such a configuration, there is an advantage that an individual tank or an individual oxygen generator does not need to be provided for each user. This kind of oxygen supply device is disclosed in Patent Documents 3 and 4.

Patent Document 1: Japanese Patent Application Laid-Open (JP-A) No. 2003-265645
Patent Document 2: JP-A No. 2007-185457
Patent Document 3: JP-A No. 2001-327602
Patent Document 4: JP-A No. 2006-328931

DISCLOSURE OF INVENTION

Problem to be Solved by the Invention

However, in the sports center or the training gym, various training machines are arranged, and users may arbitrarily use them inside the facility. Here, in the above-described configuration in which oxygen is supplied to the users through the pipe, when an oxygen mask is installed to be connected to the pipe at each training machine, the users share the same oxygen mask. That is, it is not convenient in that the oxygen mask needs to be frequently cleaned and sterilized. For this reason, it is considered that the user may not willingly use the oxygen mask since it is shared. In short, it is desirable that each user uses a private oxygen mask. Accordingly, the oxygen supply device needs to be examined in more diverse ways, taking into consideration the usage manner of the oxygen mask connected to the pipe. The invention is made in view of such circumstances, and an object thereof is to provide an oxygen supply device reasonably designed to improve convenience of a user in a facility for fitness activities.

Means for Solving the Problem

According to a first aspect of the invention, there is provided an oxygen supply device which is provided in a facility for fitness activities and supplies oxygen to users of the facility, the oxygen supply device including: an oxygen tank; a pipe which is connected to the oxygen tank; an oxygen mask; and a joint which detachably connects the oxygen mask to the pipe, in which the joint includes a socket provided for the pipe and a plug provided for the oxygen mask, wherein the oxygen mask includes a head attachment portion to be attached to a head of the user, a pipe body supported by the head attachment portion and having a front end portion extending toward the front side of the head of the user, and a tube connecting a base end portion of the pipe body to the plug, and in which the socket is provided at each important point of the pipe, and the plug is connectable to each socket.

According to a second aspect of the invention, in the oxygen supply device of the first aspect, the oxygen tank is a liquid oxygen tank or a gas oxygen tank.

According to a third aspect of the invention, in the oxygen supply device of the first aspect, a plurality of the terminal end portions of the pipes are hung on a ceiling according to an arrangement position of a training machine, and the socket is provided at each of the terminal end portions of the pipes.

Effect of the Invention

According to the invention, since each user may use the private oxygen mask and the plug provided for oxygen mask is connectable to each socket, the user may perform a fitness activity at an appropriate position corresponding to each socket. Accordingly, the oxygen supply device may remarkably improve convenience of the user of the facility.

EXPLANATION OF SYMBOLS

1: OXYGEN SUPPLY DEVICE
10: LIQUID OXYGEN TANK
20: PIPE
21: TERMINAL END PORTION
22: SHAPE HOLDING TOOL
30: OXYGEN MASK
31: HEAD ATTACHMENT PORTION
32: PIPE BODY
33: TUBE
34: OXYGEN EMISSION PORTION
40: JOINT
41: SOCKET
42: PLUG
100: FACILITY FOR FITNESS ACTIVITY
110: CEILING
210: TRAINING MACHINE
220: TRAINING MACHINE

BEST MODE(S) FOR CARRYING OUT THE INVENTION

Figure 1:
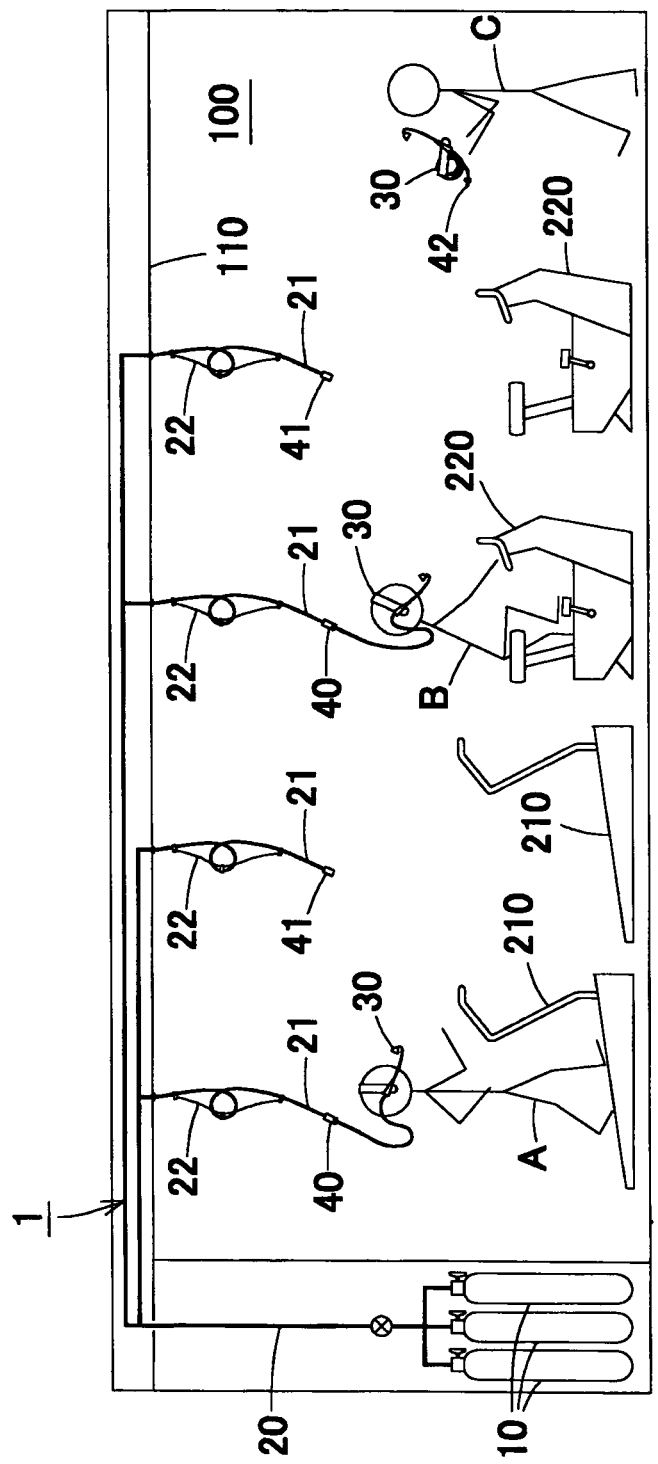
FIG. 1 is an explanatory diagram illustrating an oxygen supply device according to an embodiment of the invention.
Figure 2:
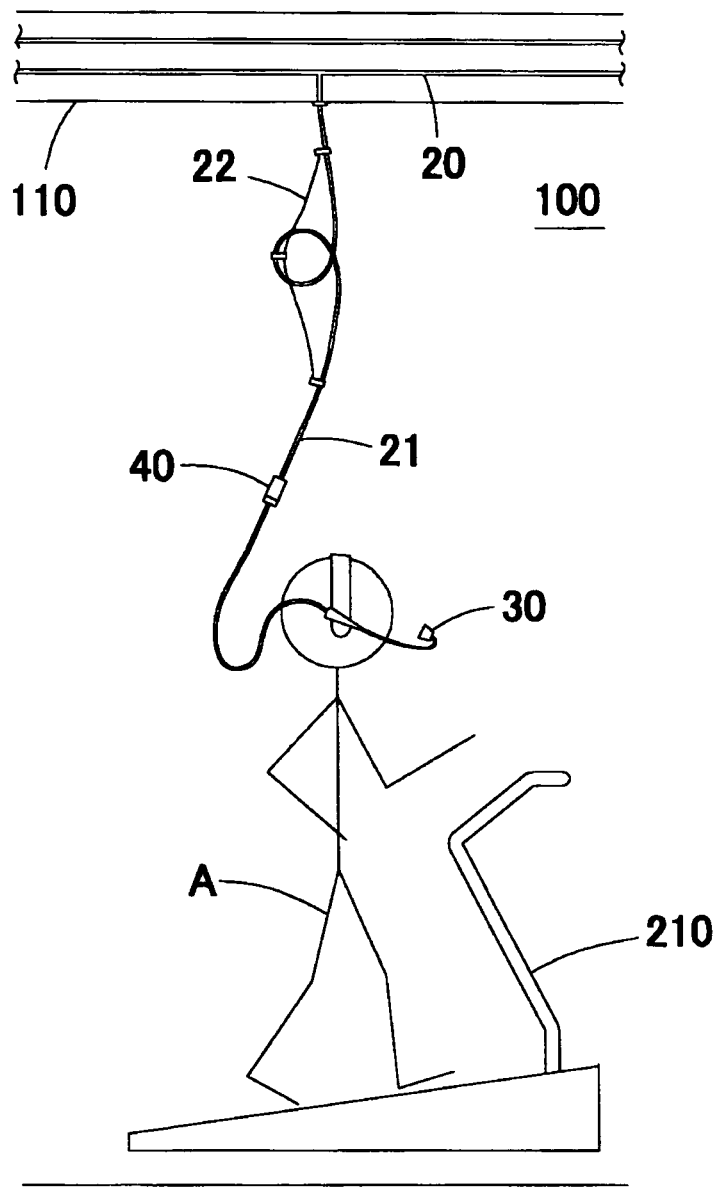
FIG. 2 is an enlarged view illustrating a main part of FIG. 1 according to the embodiment of the invention, and is an explanatory diagram illustrating the vicinity of a terminal end portion.
Figure 3:
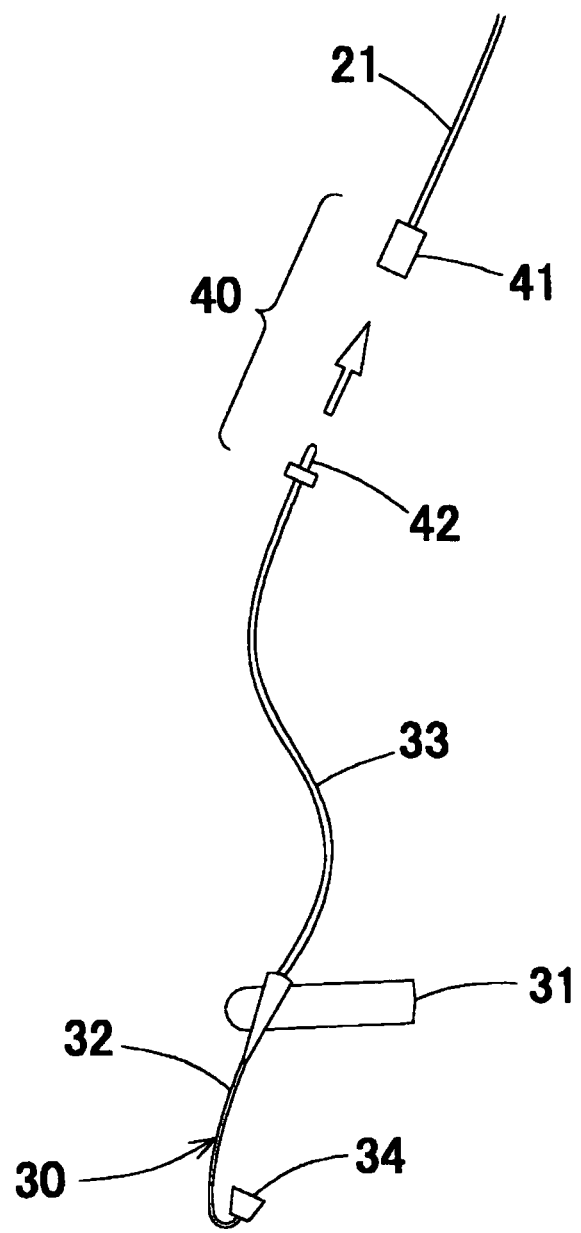
FIG. 3 is an explanatory diagram illustrating a terminal end portion of a tube, a joint, and an oxygen mask according to the embodiment of the invention.

Hereinafter, an embodiment of the invention will be described with reference to the drawings. An oxygen supply device 1 of an example shown in FIGS. 1 to 3 is provided in a facility 100 for fitness activities, and is configured to supply oxygen to each of users A, B, and C of the facility 100. Various training machines 210 and 220 are arranged in the facility 100, and the users A, B, and C may arbitrarily use them inside the facility 100.

The oxygen supply device 1 of the example includes a liquid oxygen tank 10 which is disposed at a predetermined position inside the facility 100, a pipe 20 which is connected to the liquid oxygen tank 10, an oxygen mask 30 which is portably used by the users A, B, and C, and a joint 40 which detachably connects the oxygen mask 30 to the pipe 20.

The joint 40 includes a socket 41 provided for the pipe 20 and a plug 42 provided for the oxygen mask 30. The detailed structure is not particularly limited, but the socket 41 of the example includes a hook biased by an elastic member and a spindle for opening and closing a passageway. When the plug 42 is inserted into the socket 41, the plug 42 is locked to the hook, and the spindle opens the passageway. Further, when the plug 42 is taken out from the socket 41 by releasing the locking state, the spindle closes the passageway. The socket 41 may include a flow rate adjustment unit which adjusts a flow rate of oxygen by squeezing the channel.

The oxygen mask 30 includes a head gear type head attachment portion 31 which is attached to a head of each of the users A, B, and C, a hard plastic pipe body 32 which is supported by the head attachment portion 31 and of which the front end portion extends to the front side of the head of each of the users A, B, and C, and a soft plastic tube 33 which connects a base end portion of the pipe body 32 to the plug 42. The front end portion of the pipe body 32 is provided with a predetermined-shaped oxygen emission portion 34.

In the case of the example, the socket 41 of the joint 40 is provided for each component of the pipe 20, and the plug 42 at the side of the oxygen mask 30 is configured to be connectable to each socket 41. In the example of the drawing, a plurality of terminal end portions 21 of the pipes 20 is hung on a ceiling 110 of the facility 100 in accordance with the arrangement positions of the training machines 210 and 220, and the socket 41 is provided for each of the terminal end portions 21 of the pipes 20. A shape holding tool 22 of the drawing is used to maintain the shape of the terminal end portion 21 of the pipe 20.

According to such a configuration, oxygen evaporating from the liquid oxygen tank 10 is delivered to each socket 41 through the pipe 20 by the pressure of the tank. Each of the users A, B, and C receives oxygen by connecting the plug 42 of the oxygen mask 30 carried by the user to the socket 41 corresponding to the training machines 210 and 220 in use. When the user wants to move inside the facility 100, the user carries the mask 30 by taking out the plug 42 from the socket 41. Accordingly, the oxygen mask 30 may be personalized. The configuration of the oxygen mask 30 is simple and has excellent generality for various fitness activities.

As described above, according to the configuration of the example, the oxygen supply device may be reasonably designed to improve convenience of the user of the facility.

Further, in the example, the liquid oxygen tank has been described as an oxygen tank, but the invention is not limited to the liquid oxygen tank. For example, a gas oxygen tank may be, of course, used.

Furthermore, it is needless to say that the configuration of each component in the example may be appropriately modified within the technical scope described in the claims and is not limited to the example shown in the drawings.

INDUSTRIAL APPLICABILITY

The oxygen supply device of the invention may be appropriately used as a device that supplies oxygen to a user of a sports center or a training gym.

The invention claimed is:

1. An oxygen supply device to be provided in a facility for fitness activities for supplying oxygen to a user of the facility, the oxygen supply device comprising:
   an oxygen tank;
   a pipe connected to the oxygen tank;
   an oxygen mask; and
   a joint for detachably connecting the oxygen mask to the pipe,
   wherein the joint includes a socket provided for the pipe and a plug provided for the oxygen mask,
   the oxygen mask includes a head attachment portion to be attached to a head of the user, a pipe body supported by the head attachment portion and having a front end portion extending toward a front side of the head of the user, and a tube connecting a base end portion of the pipe body to the plug,
   the joint is opened to supply oxygen to the oxygen mask when the plug is fitted to the socket,
   the joint is closed to stop supplying oxygen to the oxygen mask when the plug is detached from the socket,
   the pipe includes a plurality of terminal end portions hanging from a ceiling in accordance with an arrangement position of a training machine, and the socket is provided at each of the terminal end portions, and
   the oxygen supply device further includes a plurality of shape holding members disposed along with the terminal end portions so that each of the terminal end portions is maintained in a loop shape.

2. The oxygen supply device according to claim 1, wherein the oxygen tank is a liquid oxygen tank or a gas oxygen tank.

3. The oxygen supply device according to claim 1, wherein the terminal end portion includes a first end portion attached to the socket, and the tube includes a second end portion attached to the plug so that the tube is disconnected from the terminal end portion when the plug is detached from the socket.

4. The oxygen supply device according to claim 1, wherein the socket includes a spindle for opening the joint when the plug is fitted to the socket, and closing the joint when the plug is detached from the socket.

5. The oxygen supply device according to claim 1, wherein each of the shape holding members is attached to each of the terminal end portions at a middle of the loop shape.

* * * * *